(12) United States Patent
Orbay et al.

(10) Patent No.: US 10,617,454 B2
(45) Date of Patent: Apr. 14, 2020

(54) ARTICULATED FRACTURE FIXATION PLATE ASSEMBLY AND METHOD OF USE

(71) Applicant: Skeletal Dynamics, LLC, Miami, FL (US)

(72) Inventors: Jorge L. Orbay, Miami, FL (US); Alexander Gil, Miami, FL (US)

(73) Assignee: Skeletal Dynamics, Inc., Miami, FL (US)

( * ) Notice: Subject to any disclaimer, the term of this patent is extended or adjusted under 35 U.S.C. 154(b) by 23 days.

(21) Appl. No.: 16/003,366

(22) Filed: Jun. 8, 2018

(65) Prior Publication Data

US 2019/0133652 A1    May 9, 2019

Related U.S. Application Data

(60) Provisional application No. 62/517,010, filed on Jun. 8, 2017.

(51) Int. Cl.
*A61B 17/80* (2006.01)
*A61B 17/00* (2006.01)

(52) U.S. Cl.
CPC ...... *A61B 17/8061* (2013.01); *A61B 17/8057* (2013.01); *A61B 2017/00477* (2013.01)

(58) Field of Classification Search
CPC .. A61B 17/80; A61B 17/8061; A61B 17/8023
USPC .......................................................... 606/71
See application file for complete search history.

(56) References Cited

U.S. PATENT DOCUMENTS

| | | | |
|---|---|---|---|
| 9,956,015 B2* | 5/2018 | Ehmke | A61B 17/8057 |
| 2003/0114856 A1* | 6/2003 | Nathanson | A61B 17/8009 606/70 |
| 2004/0102778 A1 | 5/2004 | Huebner et al. | |
| 2006/0089648 A1* | 4/2006 | Masini | A61B 17/1615 606/71 |
| 2006/0241597 A1* | 10/2006 | Mitchell | A61F 2/4684 606/247 |
| 2011/0022049 A1* | 1/2011 | Huebner | A61B 17/1728 606/71 |
| 2011/0218534 A1 | 9/2011 | Prandi et al. | |
| 2013/0060288 A1* | 3/2013 | Rodgers | A61B 17/1604 606/281 |
| 2014/0081269 A1 | 3/2014 | Biedermann | |
| 2015/0173812 A1 | 6/2015 | Masson | |
| 2016/0000481 A1 | 1/2016 | Ehmke et al. | |
| 2016/0058481 A1 | 3/2016 | Blain et al. | |
| 2016/0135859 A1 | 5/2016 | Mootien et al. | |
| 2016/0262812 A1* | 9/2016 | May | A61B 17/1728 |

* cited by examiner

*Primary Examiner* — David W Bates
(74) *Attorney, Agent, or Firm* — Lott & Fischer, PL (57) ABSTRACT

Disclosed is a fracture fixation plate assembly comprised of a body, a hinge, a pin, and one or more heads, in which the head or heads can pivot and displace laterally/medially and can tilt vertically with respect to the body of the plate, more efficiently and flexibly enabling the fastening of the body of the plate to a stable part of the bone prior to reduction of the fractured portion or portions of the bone.

11 Claims, 10 Drawing Sheets

ARTICULATED FRACTURE FIXATION PLATE ASSEMBLY AND METHOD OF USE

CLAIM OF PRIORITY

This application is being filed as a non-provisional patent application under 35 U.S.C. § 111(a) and 37 CFR § 1.53(b). This application claims priority under 35 U.S.C. § 119(e) to U.S. provisional patent application Ser. No. 62/517,010 filed on Jun. 8, 2017, the contents of which are incorporated herein by reference.

FIELD OF INVENTION

The invention relates generally to the fixation of bone fractures and in particular to plates for the fixation of fractures of the distal radius or other bones of the human body.

BACKGROUND OF THE INVENTION

Fracture fixation plates for the distal radius are known in the art. In particular, volar fracture fixation plates for the treatment of the Colles' fracture are frequently used. While many existing plates are effective, they generally require that the fracture in the distal radius be reduced prior to application and fastening of the plate.

SUMMARY OF THE INVENTION

It is among the objects of this invention to overcome the limitations of the heretofore-known devices by providing inventive features to achieve a volar fixation plate comprised of a body and one or more heads, in which the head or heads can pivot and displace laterally/medially and tilted vertically with respect to the body of the plate. This would enable the attachment of the heads to the unstable distal end of the bone or bone fragments, manipulation of the heads to align the unstable bone and fragments, fastening of the body of the plate to a stable part of the bone, reduction of the fractured portion or portions of the bone, and once reduction is achieved, locking of the position of the plate to maintain the achieved reduction.

Although the invention is illustrated and described herein as embodied in a volar fracture fixation plate for the distal radius it is nevertheless not intended to be limited to only the details shown, or even to a plate designed to treat volar fractures, since various modifications and structural changes may be made therein to achieve fixation of fractures in other bones of the body without departing from the spirit of the invention and within the scope and range of equivalents of the claims.

The construction of the invention, however, together with additional objects and advantages thereof will be best understood from the following description of the specific disclosed embodiments when read in connection with the accompanying drawings.

DETAILED DESCRIPTION OF THE INVENTION

Figure 1:
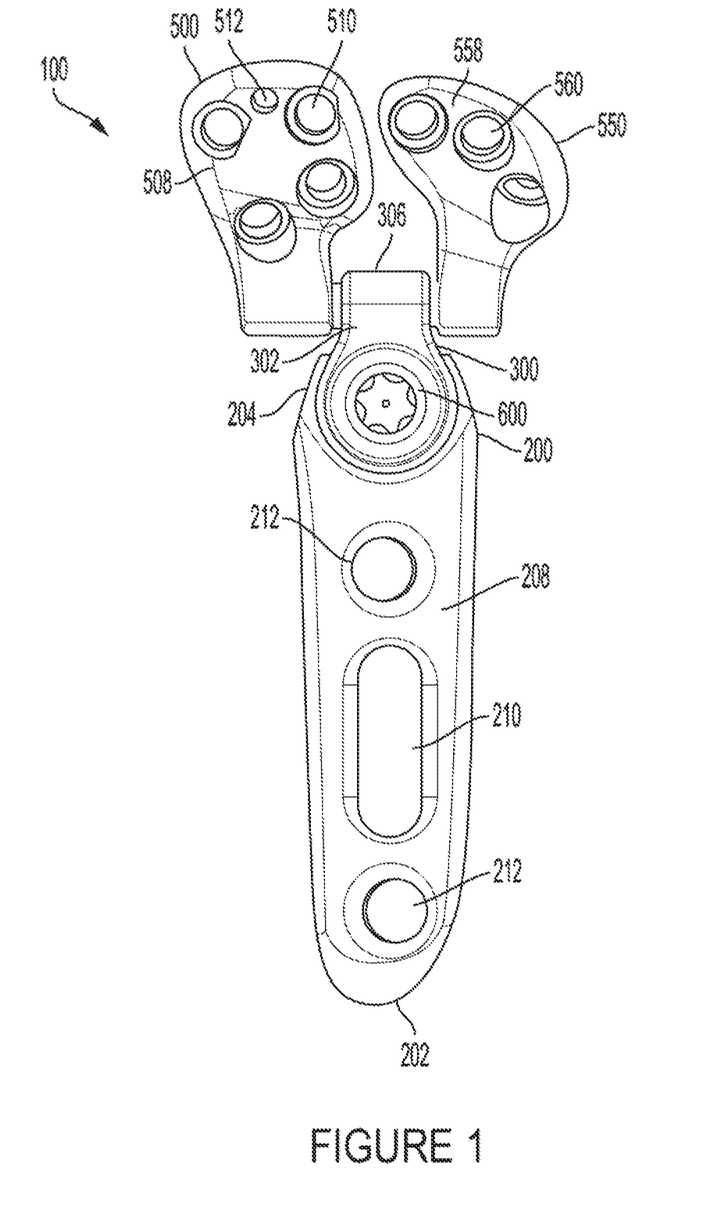
FIG. 1 is a top view of a dual-head fracture fixation plate assembly in accordance with the present invention with the heads in the neutral centered position.
Figure 2:
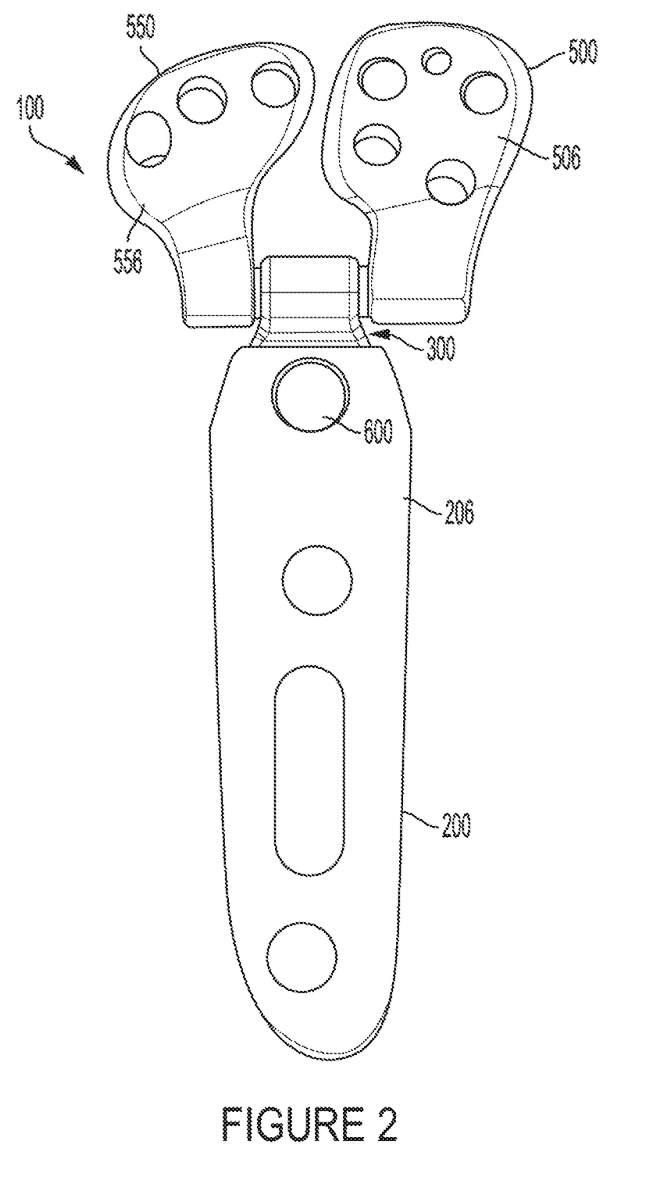
FIG. 2 is a bottom view of a dual-head fracture fixation plate assembly in accordance with the present invention with the heads in the neutral centered position.
Figure 3:
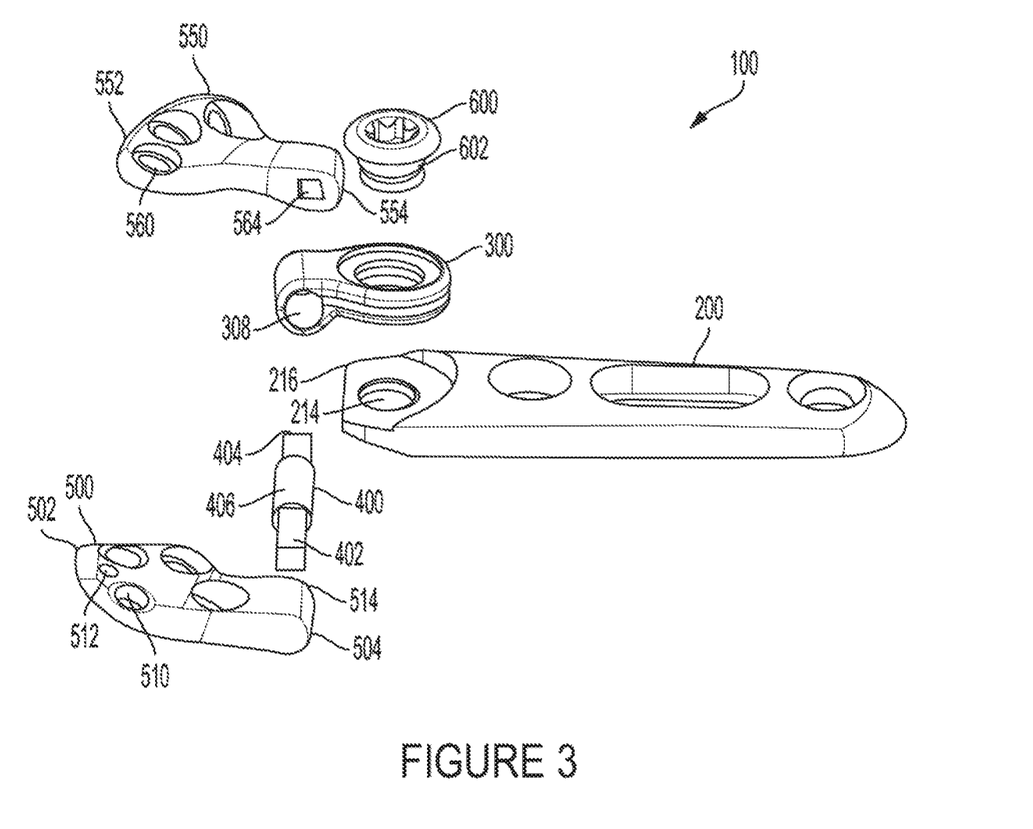
FIG. 3 is an exploded view of a dual-head fracture fixation plate assembly in accordance with the present invention.
Figure 4:
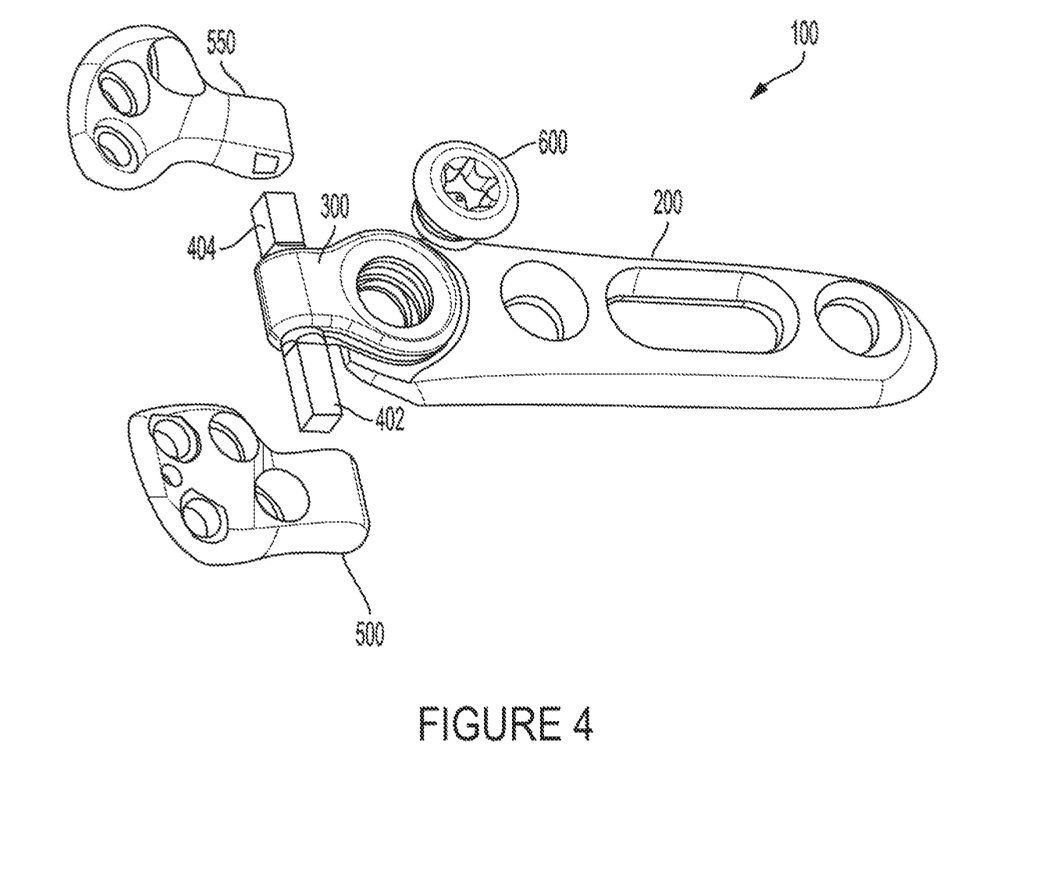
FIG. 4 is a partially assembled view of a dual-head fracture fixation plate assembly in accordance with the present invention.

Referring to FIGS. 1 and 2, in one embodiment of the present invention, a generally "Y" shaped fracture fixation plate assembly 100 is shown in top and bottom views respectively. The various components of the assembly 100 can be seen in greater detail in FIGS. 3 and 4 which respectively show exploded and partially exploded views of assembly 100. As can be seen in FIG. 3, the various separate components of assembly 100 include a body 200, a hinge 300, an axle 400, an ulnar head 500, a radial head 550, and a setting fastener 600.

Body 200 is a substantially straight, or slightly curved, elongated component having a bone contacting surface 206 and an opposite surface 208, a proximal end 202, a distal end 204, and at least one anchoring slot 210 or hole 212 adapted to receive a bone fastener. Distal end 204 of body 200 also comprises a threaded hole 214 adapted to receive setting fastener 600.

Axle (or pin) 400 comprises an elongated solid pin, including an ulnar end 402, a radial end 404 and a middle section 406. The ulnar and radial ends 402,404 have non-circular cross sections designed to mate with correspondingly shaped openings in the ulnar head 500 and radial head 550 respectively. The middle section 406 is substantially cylindrical as it is intended to engage a corresponding barrel 308 in hinge 300 (see FIG. 5 and below description thereof.)

Figure 5:
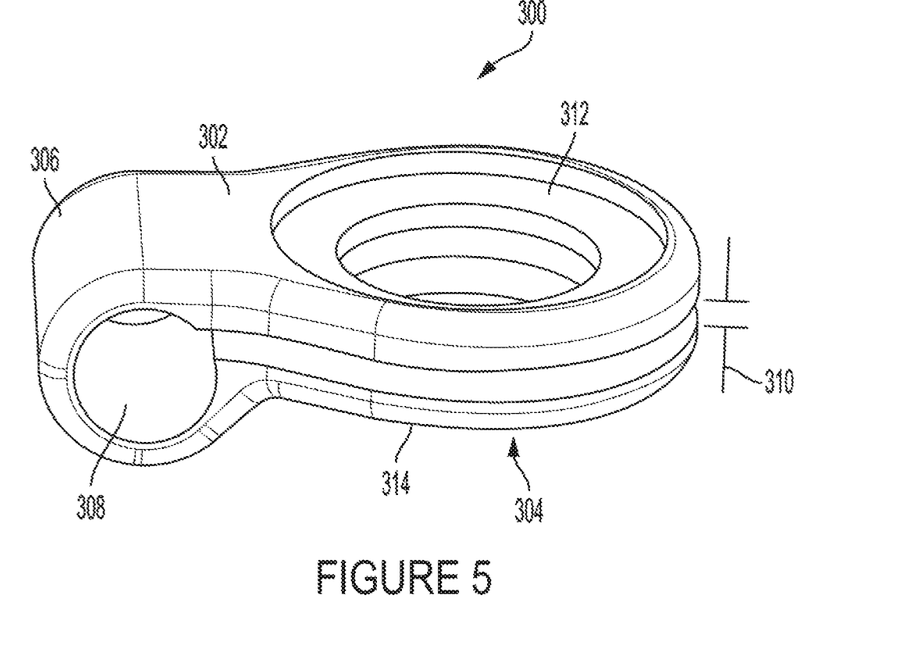
FIG. 5 is a detailed view of a hinge component for a dual-head fracture fixation plate assembly in accordance with the present invention.

Referring momentarily to FIG. 5, hinge 300 is shown in greater detail. Hinge 300 comprises a clamp having a top side 302, a bottom side 304, and a bridge 306 connecting the top side 302 and bottom side 304. The top and bottom sides 302,304 each have equally sized holes 312,314 which are aligned and have a diameter that is greater than that of the shaft 602 of setting fastener 600. The inside surface of bridge 306 defines a substantially cylindrical barrel 308 which is adapted to receive the middle section 406 of axle 400. In its unlocked state (which is shown in FIG. 5), a gap 310 exists between the top and bottom sides 302,304, and the diameter of barrel 308 is larger than the diameter of axle middle section 406. This allows axle 400 to freely rotate inside barrel 308 and also to freely translate from side to side with respect to barrel 308.

Referring back to FIGS. 1-5, hinge 300 is adapted to attach to distal end 204 of body 200 by means of setting fastener 600. As will be noted, upon engagement of setting fastener 600 through hinge holes 312,314 and into threaded hole 214 of body 200, hinge 300 will be in its unlocked state. As setting fastener 600 is tightened, hinge 300 will begin to compress and the diameter of barrel 308 will begin to diminish. As setting fastener 600 is tightened, the friction between axle middle section 406 and barrel 308 increases, making it more difficult for axle 400 to rotate or translate. When setting fastener 600 is fully tightened, axle 400 is essentially in a fixed position and cannot rotate or translate with respect to hinge 300.

In addition, it will be noted that upon initial insertion of setting fastener 600, hinge 300 is free to pivot about threaded hole 214 of body 200. As setting fastener 600 is tightened, the friction between the bottom side 304 of hinge 300 and bearing area 216 surrounding threaded hole 214 increases, making it more difficult for hinge 300 to pivot with respect to body 200. When setting fastener 600 is fully tightened, hinge 300 is essentially in a fixed position and cannot pivot with respect to body 200.

Ulnar head 500 comprises a distal end 502, a proximal end 504, a bone contacting surface 506 and an opposite surface 508. Ulnar head 500 further includes one or more bone screw holes 510 (which can be threaded or unthreaded) and optionally one or more K-wire holes 512. The proximal end 504 of ulnar head 500 further comprises axle opening 514 which is adapted to receive ulnar end 402 of axle 400. Axle ulnar end 402 fits snugly within axle opening 514. Upon assembly ulnar head 500 and axle 400 are permanently connected via an interference fit, one or more fasteners, one or more welds, or other methods known in the art.

Similar to Ulnar head 500, radial head 550 comprises a distal end 552, a proximal end 554, a bone contacting surface 556 and an opposite surface 558. Radial head 550 further includes one or more bone screw holes 560 (which can be threaded or unthreaded) and optionally one or more K-wire holes 562. The proximal end 554 of ulnar head 550 further comprises axle opening 564 which is adapted to receive radial end 404 of axle 400. Axle radial end 404 fits snugly within axle opening 564. Upon assembly radial head 550 and axle 400 are permanently connected via an interference fit, one or more fasteners, one or more welds, or other methods known in the art.

Figure 6A:
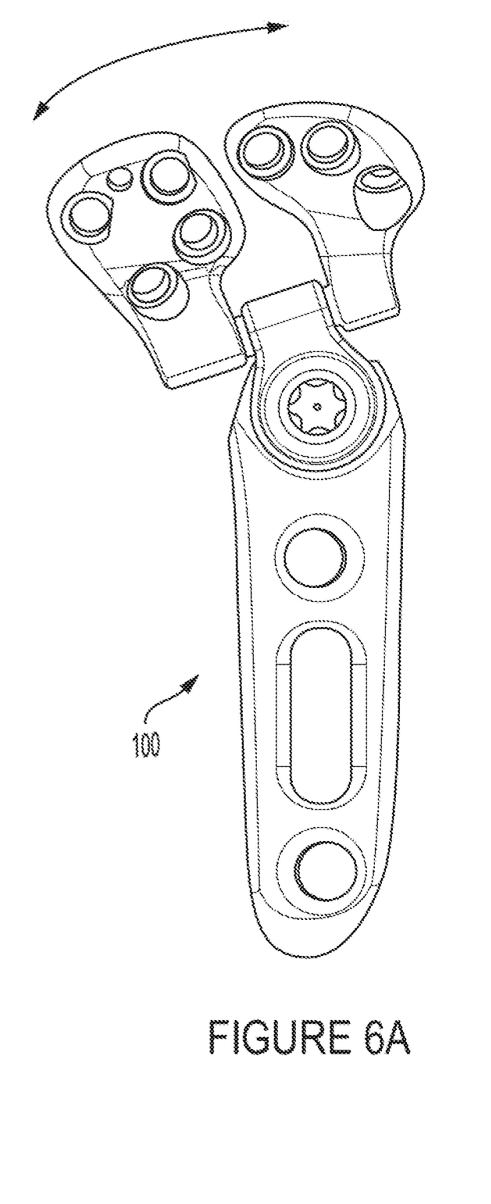
FIGS. 6A and 6B are top views of a dual-head fracture fixation plate assembly in accordance with the present invention with the heads pivoted in the medial and lateral direction respectively.
Figure 6B:
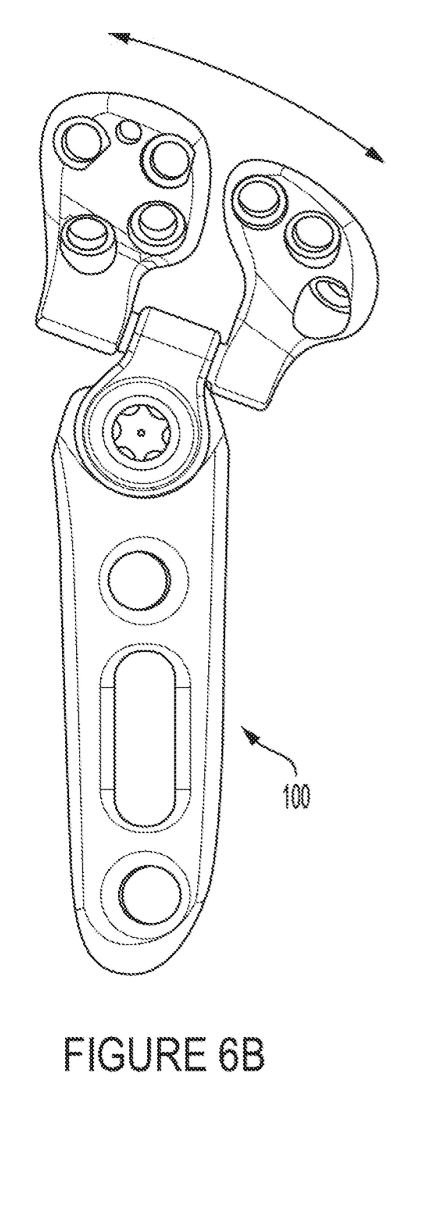
Figure 7A:
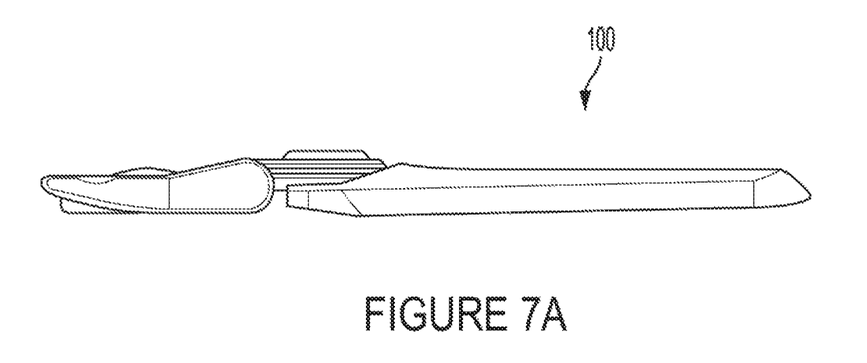
FIGS. 7A and 7B are medial side views of a dual-head fracture fixation plate assembly in accordance with the present invention with the heads in the neutral position and tilted vertically upwards respectively.
Figure 7B:
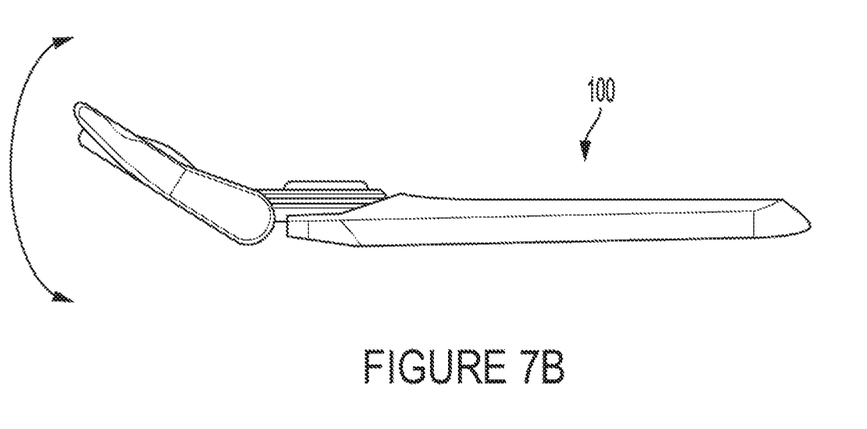
Figure 8A:
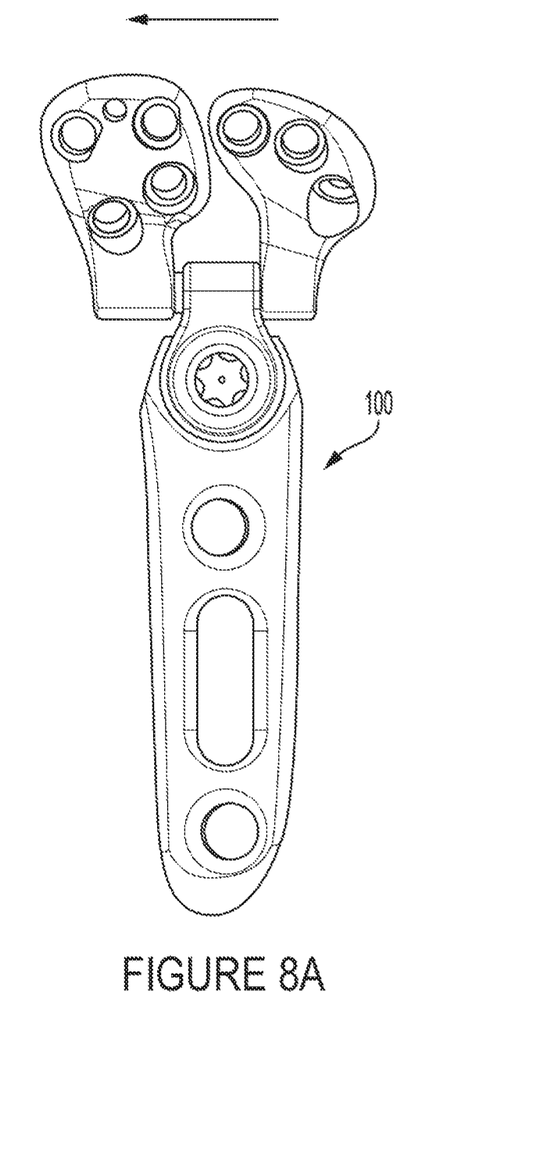
FIGS. 8A and 8B are top views of a dual-head fracture fixation plate assembly in accordance with the present invention with the heads translated in the medial and lateral direction respectively.
Figure 8B:
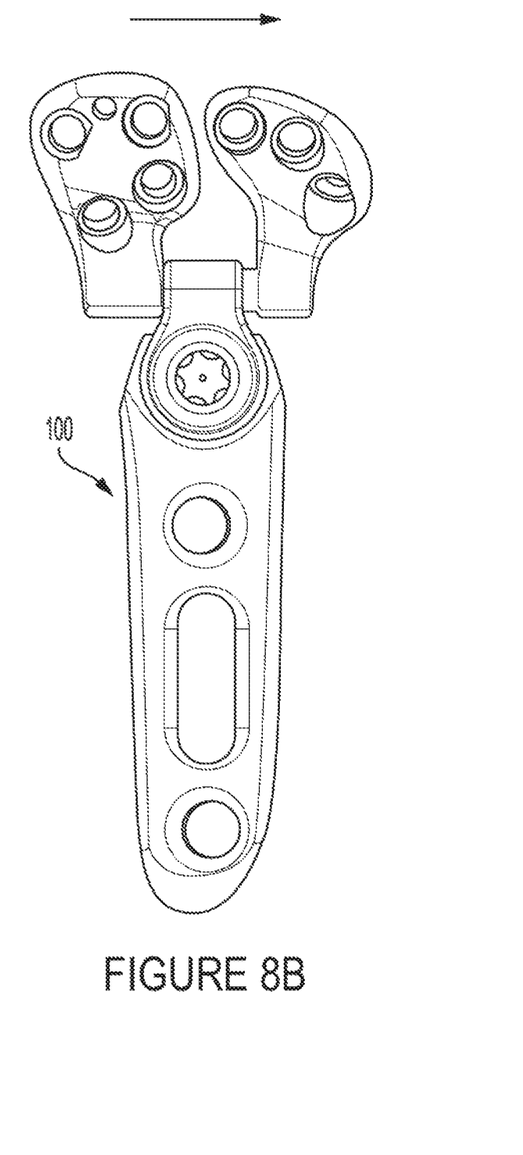

Upon full assembly of the device of the present invention, as shown in FIGS. 1 and 2, fracture fixation plate assembly 100 will enable a head or a plurality of heads to pivot laterally in the medial/lateral direction (see FIGS. 6A and 6B), tilt upward and downward (see FIGS. 7A and 7B), and translate in the medial/lateral direction (see FIGS. 8A and 8B). Each of the configurations shown in FIGS. 6-8 can be adjusted by loosening setting screw 600 and manually repositioning the ulnar and radial heads 500, 550. Upon tightening of setting screw 600, the selected configuration becomes fixed.

Figure 9:
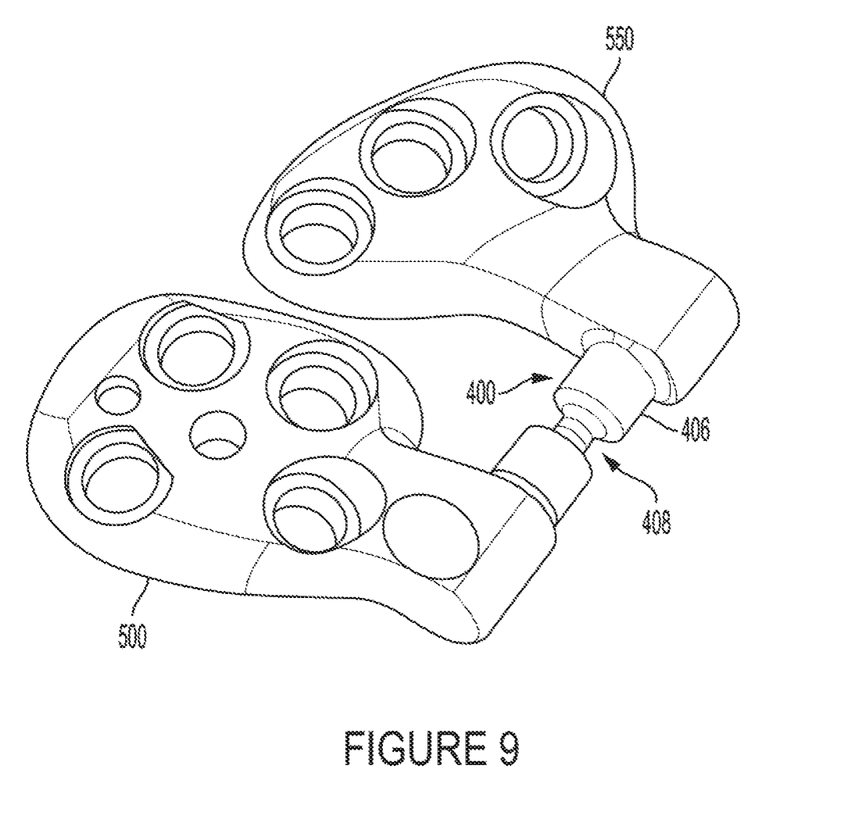
FIG. 9 shows an axle and head assembly for an alternative embodiment of a dual-head fracture fixation plate assembly in accordance with the present invention.
Figure 10:
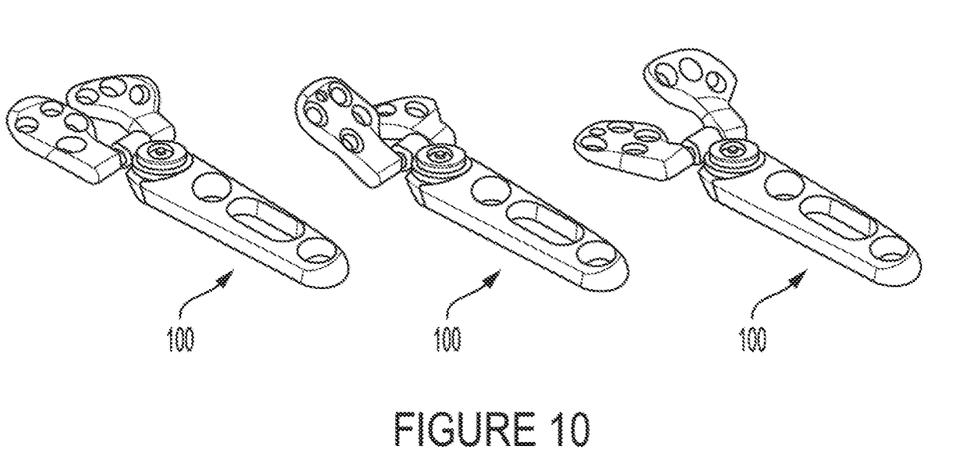
FIG. 10 shows a dual-head fracture fixation plate assembly in accordance with the present invention with the heads tilted (i.e.: rotated) into multiple configurations, including configurations with the heads tilted independently of each other.

In an alternative embodiment of the present invention shown in FIG. 9, the middle section 406 of axle 400 may also comprise a narrowed neck section 408. This narrowed neck section would torsionally weaken axle 400. This would enable the pivoting of ulnar head 500 and radial 550 independent of each other by the partial deformation of axle 400 through the application of torque. Some of the resulting possible configurations are shown in FIG. 10.

As previously described above, the instant invention provides a fracture fixation plate with a hinge component and a plurality of head portions, interconnecting to a pin component. This is particularly advantageous for permitting the application of the fracture fixation plate prior to reducing the fracture.

A method for using the fracture fixation plate assembly of the present invention for reducing a bone fracture comprises: placing the fracture fixation plate assembly in the unlocked state in close proximity to the fractured bone so that the bone contacting surface of at least one head is adjacent to a fractured portion of the bone; attaching the at least one head to the fractured portion of the bone using at least one bone fastener through at least one hole of the head; loosely attaching the body portion to the main portion of the bone using at least one anchoring fastener through an anchoring slot on the body portion; manipulating the head by pivoting, rotating and translating the head to align the fractured portion of the bone with a main portion of the bone; adjusting as needed the tilt of the head relative to the body portion; reducing the fracture by moving the fracture fixation plate with respect to the main portion of the bone; fixing the body portion to the main portion of the bone by fastening the anchoring fastener to the main portion of the bone; and transitioning the fracture fixation plate assembly to the locked state by fastening the setting fastener.

Although described above in connection with a volar fracture fixation plate assembly and method of use for the distal radius, these descriptions are not intended to be limiting, as other plates can be made in accordance with the description herein, but of different size or scale, so as to treat other fractures, as desired. As such, although the invention is illustrated and described herein, various modifications and structural changes may be made therein without departing from the spirit of the invention and within the scope and range of equivalents of the claims.

We claim:

1. A fracture fixation plate assembly comprising:
    an elongated body defining a first longitudinal axis and including a proximal end, a distal end, a bone contacting surface, an opposite surface, at least one anchoring slot extending from said bone contacting surface to said opposite surface and a pivot hole at said distal end;
    a hinge, including a proximal end and a distal end, the proximal end pivotally engaged with the distal end of said body defining a first pivot axis transverse to said first longitudinal axis and the distal end of the hinge including a substantially cylindrical barrel, said barrel defining a second pivot axis transverse to both said longitudinal axis and said first pivot axis; said hinge having an unlocked state and a locked state;
    a setting fastener, adapted for insertion along said first pivot axis of said hinge and into said pivot hole of said elongated body, wherein when said setting fastener is loose, said hinge remains in an unlocked state and when said setting fastener is tightened said hinge remains in a locked state;
    an axle adapted to be received by the cylindrical barrel of said hinge, having a lateral end, a medial end, and a middle portion defining an axle axis, the middle portion pivotally engaged with said barrel of said hinge, said axle axis collinear with said second pivot axis and at least one of said lateral or medial ends extending out from said barrel of said hinge; and at least one head having a bone contacting surface and an opposite surface, said at least one head rigidly engaged to said lateral and/or medial end of said axle, and said at least one head having at least one hole adapted to receive a bone fastener said hole extending from said bone contacting surface to said opposite surface;

wherein said body, hinge, setting fastener, axle and at least one head are separate components;

wherein, in the unlocked state, said hinge is adapted to pivot laterally/medially with respect to said body around said first pivot axis;

wherein, in the unlocked state, said axle is adapted to displace laterally/medially along said second pivot axis and to rotate in said cylindrical barrel about said second pivot axis;

wherein, in the locked state, said hinge is impeded from pivoting with respect to said body; and wherein, in the locked state, said axle is impeded from displacing along, and rotating about, said second pivot axis.

2. The fracture fixation plate assembly of claim 1 wherein:
said middle section of said axle further comprises a narrowed neck section; and
said narrowed neck section is adapted to enable said lateral end to rotate independently of said medial end through at least partial deformation of said neck section.

3. A method for reducing a bone fracture using the fracture fixation plate assembly of claim 1 comprising the steps, not necessarily in sequence, of:
placing said fracture fixation plate assembly in the unlocked state in close proximity to the fractured bone so that said bone contacting surface of said at least one head is adjacent to a fractured portion of said bone;
attaching the at least one head to said fractured portion of said bone using said at least one bone fastener through said at least one hole of said at least one head;
loosely attaching said body portion to said main portion of said bone using at least one anchoring fastener through said at least one anchoring slot;
manipulating said at least one head by pivoting, rotating and translating said at least one head to align said fractured portion of said bone with a main portion of said bone;
adjusting the tilt of said at least one head relative to said body portion;
reducing said fracture by moving said fracture fixation plate with respect to said main portion of said bone;
fixing said body portion to said main portion of said bone by fastening said at least one anchoring fastener to said main portion of said bone; and
transitioning said fracture fixation plate assembly to said locked state by fastening said setting fastener.

4. The fracture fixation plate assembly of claim 1 wherein:
said hinge comprises a clamp about the cylindrical barrel, wherein tightening of said setting fastener tightens said clamp and secures the displacement and rotational position of said axle within the cylindrical barrel.

5. The fracture fixation plate assembly of claim 4 wherein:
said hinge comprises a top side and a bottom side separated by a gap, wherein said top side and said bottom side are connected via a bridge substantially around and defining the cylindrical barrel, wherein tightening of said setting fastener diminishes the size of said gap and decreases the diameter of the cylindrical barrel, securing the displacement and rotational position of said axle within the cylindrical barrel.

6. The fracture fixation plate assembly of claim 1 wherein:
said elongated body comprises a substantially flat bearing area on the opposite surface about said pivot hole, the bearing area recessed towards said bone contacting surface, wherein said bearing area is adapted for engaging the surface of the proximal end of the hinge and providing friction between said hinge and said elongated body to secure the pivotal position of the hinge with respect to the elongated body in the locked state.

7. The fracture fixation plate assembly of claim 1 wherein:
said at least one head further comprises at least one K-wire hole adapted to receive a K-wire, said hole extending from said bone contacting surface to said opposite side.

8. The fracture fixation plate assembly of claim 1 wherein:
said at least one head is permanently connected to said lateral and/or medial end of said axle via an interference fit.

9. The fracture fixation plate assembly of claim 1 wherein:
said at least one head is permanently connected to said lateral and/or medial end of said axle via one or more fasteners.

10. The fracture fixation plate assembly of claim 1 wherein:
said at least one head is permanently connected to said lateral and/or medial end of said axle via one or more welds.

11. The fracture fixation plate assembly of claim 1 wherein:
said lateral and medial ends of said axle comprise a non-circular cross section adapted for mating with a corresponding opening in said at least one head.

* * * * *